(12) United States Patent
Perier et al.

(10) Patent No.: US 9,763,867 B2
(45) Date of Patent: Sep. 19, 2017

(54) PHOTOPROTECTIVE SYSTEM

(71) Applicant: PIERRE FABRE DERMO-COSMETIQUE, Boulogne-Billancourt (FR)

(72) Inventors: Valérie Perier, Frouzins (FR); Hélène Dromigny, Toulouse (FR)

(73) Assignee: PIERRE FABRE DERMO COSMETIQUE, Boulogne-Billancourt (FR)

( * ) Notice: Subject to any disclaimer, the term of this patent is extended or adjusted under 35 U.S.C. 154(b) by 14 days.

(21) Appl. No.: 14/375,664

(22) PCT Filed: Jan. 30, 2013

(86) PCT No.: PCT/EP2013/051776
§ 371 (c)(1),
(2) Date: Jul. 30, 2014

(87) PCT Pub. No.: WO2013/113745
PCT Pub. Date: Aug. 8, 2013

(65) Prior Publication Data
US 2015/0050223 A1    Feb. 19, 2015

(30) Foreign Application Priority Data

Jan. 31, 2012   (FR) ...................................... 12 50872

(51) Int. Cl.
| A61K 8/49 | (2006.01) |
| A61K 8/37 | (2006.01) |
| A61K 8/35 | (2006.01) |
| A61K 8/29 | (2006.01) |
| A61Q 17/04 | (2006.01) |

(52) U.S. Cl.
CPC .............. *A61K 8/4973* (2013.01); *A61K 8/29* (2013.01); *A61K 8/35* (2013.01); *A61K 8/37* (2013.01); *A61K 8/496* (2013.01); *A61K 8/4946* (2013.01); *A61K 8/4966* (2013.01); *A61Q 17/04* (2013.01)

(58) Field of Classification Search
None
See application file for complete search history.

(56) References Cited

U.S. PATENT DOCUMENTS

| 2008/0267892 A1* | 10/2008 | Picoul ................ C07D 253/065 424/59 |
| 2011/0250248 A1 | 10/2011 | Omura et al. |
| 2012/0128610 A1 | 5/2012 | Nazarova et al. |
| 2012/0276027 A1* | 11/2012 | Kessler ................ A61K 8/8182 424/59 |

FOREIGN PATENT DOCUMENTS

| DE | WO 2011086073 A2 * | 7/2011 | .......... A61K 8/8182 |
| EP | 1 764 081 A1 | 3/2007 | |
| EP | 1 955 691 A1 | 8/2008 | |
| EP | 2 179 986 A1 | 4/2010 | |
| EP | 2 243 517 A1 | 10/2010 | |
| FR | WO 2005121128 A1 * | 12/2005 | ......... C07D 253/065 |
| FR | WO 2009027390 A2 * | 3/2009 | ............... A61K 8/35 |
| WO | WO 2005/121128 A1 | 12/2005 | |
| WO | WO 2009/027390 A2 | 3/2009 | |
| WO | WO 2009/092972 A2 | 7/2009 | |
| WO | WO 2011/070053 A2 | 6/2011 | |
| WO | WO 2011/086073 A2 | 7/2011 | |

OTHER PUBLICATIONS

Tinosorb A2B product sheet [downloaded on Nov. 18, 2015 from the Google translation of the website http://www.ulprospector.com/en/eu/PersonalCare/Detail/804/237766/Tinosorb-A2B?st=20 ].*
CIBA's "Time and Extent Application" for Bemotrizinol 2005.*
Tinosorb A2B product sheet.*
Tinosorb A2B product sheet 2015.*
French Search Report dated Dec. 6, 2012, for French Application No. 1250872.
International Search Report, mailed Jan. 3, 2014, issued in PCT/EP2013/051776.

* cited by examiner

*Primary Examiner* — Robert A Wax
*Assistant Examiner* — Thor Nielsen
(74) *Attorney, Agent, or Firm* — Birch, Stewart, Kolasch & Birch, LLP

(57) ABSTRACT

The present invention concerns a topical, cosmetic or pharmaceutical preparation containing a combination of 3 or 4 solar filters comprising:—one or two UVA filters to obtain a critical wavelength>370 nm, chosen from among: (i)—5,6, 5,6-tetraphenyl-3, 3'-(1,4-phenylene)-bis[1,2,4]triazine; (ii) 1,1'-(1,4-piperazinediyl)bis[1-[2-[4-(diethylamino)-2-hydroxybenzoyl]phenyl]-methanone; (iii)—Butyl Methoxydibenzoylmethane (BMDBM), in a quantity less than 2% by weight with regard to the total weight of said composition; (iv)—Hexyl-[4-(diethylamino)-2-hydroxybenzoyl]benzoate, -2,4-Bis[4-(2-ethyl-hexyloxy)-2-hydroxyphenyl]-6-(4-methoxyphenyl)-1,3,5-triazine=(BEMT), —one or two filters chosen from among UVB filters, except octocrylene, PABA and ethylhexyl methoxycinnamate, said composition also containing a pharmaceutically or cosmetically acceptable excipient.

25 Claims, No Drawings

PHOTOPROTECTIVE SYSTEM

The present invention relates to a combination of solar filters useful as a photoprotective system in cosmetic or pharmaceutical compositions.

First of all, we will review below the nomenclature and abbreviations of the various filters involved in the scope of the present invention:

UVA Filters
  5,6,5,6-tetraphenyl-3,3'-(1,4-phenylene)-bis[1,2,4]triazine described in WO2005/121128;
  Hexyl 2-[4-(diethylamino)-2-hydroxybenzoyl]benzoate=CAS Registry Number: 302776-68-7 which filter is sold as Uvinul A+® by BASF;
  Methanone, 1,1'-(1,4-piperazinediyl)bis[1-[2-[4-(diethylamino)-2-hydroxy benzoyl]phenyl]-=CAS Registry Number: 919803-06-8 which is sold as C1332® by BASF;
  Butyl Methoxydibenzoylmethane (BMDBM)=avobenzone=CAS Registry Number: 70356-09-1 which is sold as Parsol1789® by DSM.

UVB Filters
  Diethylhexyl Butamido Triazone=CAS Registry Number: 154702-15-5 which is sold as UVASorb HEB® by 3V SIGMA;
  2,4,6-tris([1,1'-biphenyl]-4-yl)-1,3,5-triazine=tris-biphenyl triazine=CAS Registry Number: 31274-51-8 which is sold as ETH50® by BASF;
  Octyl triazone=ethylhexyl triazone=CAS Registry Number: 88122-99-0 which is sold as UvinulT150® by BASF.
  2-phenylbenzimidazole-5-sulfonic acid=phenylbenzimidazole sulfonic acid=CAS Registry Number 27503-81-7
  2-ethylhexyl salicylate=ethylhexyl salicylate=CAS Registry Number 118-60-5

Broad Spectrum Filters
  2,2'-Methylene-bis-(6-(2H-benzotriazole-2-yl)-4-(1,1,3,3-tetramethylbutyl)-phenol=Methylene Bis-Benzotriazolyl Tetramethylbutylphenol (MBBT)=Bisoctrizole=CAS Registry Number: 103597-45-1 which is sold as Tinosorb M® by BASF;
  2,4-Bis[4-(2-ethylhexyloxy)-2-hydroxyphenyl]-6-(4-methoxyphenyl)-1,3,5-triazine=Bis-Ethylhexyloxyphenol Methoxyphenyl Triazine (BEMT)=Bemotrizinol=CAS Registry Number: 187393-00-6 which is sold as Tinosorb S® by BASF.

We will briefly remind you that the action of solar radiation on the skin basically depends on the energy of the radiation that reaches the various skin layers. Generally, the most energetic radiation, that is having the shortest wavelength ($E=hc/l$), induces erythema or sunburn, while less energetic radiation simply causes the skin to tan. It is therefore believed that a sun filter, intended to be used in the composition of cosmetic preparations called sunscreens must maximally absorb short wavelength radiation, while remaining transparent to longer wave radiation.

Usually UV-A and UV-B are distinguished, corresponding to decreasing wavelengths respectively comprised between 400 nm and 320 nm, and between 320 nm and 280 nm. UV-B and UV-A allow the human epidermis to tan. UV-B causes erythema and skin burns that can be harmful to the development of natural tanning. For these reasons, as well as for esthetic reasons, there is a constant demand for a means for controlling this natural tanning in order to control the color of the skin. Therefore, UV-B radiation should be filtered.

It is also known that UV-A radiation can cause skin changes, especially in the case of sensitive skin or skin continuously exposed to solar radiation. UV-A radiation particularly causes a loss of elasticity of the skin and the appearance of wrinkles, leading to premature aging. It triggers erythematous reactions or amplifies these reactions in some subjects and may even be the cause of phototoxic or photoallergic reactions. It is therefore desirable to also filter UV-A.

Furthermore, it has also been established that exposure to ultraviolet radiation, by sun exposure or the use of sun lamps for tanning, is the main cause of skin cancers.

Finally, some anti-UV filters described in the prior art are currently known to be responsible for allergic reactions (contact eczema) and/or suspected systemic toxicity (able to act as an endocrine disruptor, among other things).

There is therefore a real need to develop photoprotective systems that can effectively filter ultraviolet radiation and overcome the disadvantages of intolerance and toxicity encountered.

Therefore, we are careful not to use UV filters deemed unsatisfactory from the tolerance and/or toxicity and/or photostabilization and/or low UV absorption point of view such as
  Octocrylene,
  Para-aminobenzoic acid (PABA),
  Ethylhexyl methoxycinnamate;
Preferably, the composition according to the invention will not contain
  Octocrylene
  PABA and its derivatives
  The cinnamate chemical family, including ethylhexyl methoxycinnamate;
  The benzophenone family and
  The benzylidene camphor family
  And, as a precaution, homosalate.

"Photoprotective system", in the sense of the present invention, means any compound or combination of compounds that allows, after application onto a surface (skin, hair, etc.) by mechanisms of absorption and/or reflection and/or diffusion of UV-A and/or UV-B radiation, preventing or at least limiting the contact of said radiation with said surface.

The term "ultraviolet radiation" means solar ultraviolet radiation and artificial ultraviolet radiation (tanning lamps, for example).

The technical characteristics and expected advantages of the novel photoprotective system according to the present invention are the following:
  The broadest possible UV absorption spectrum (maximum spectral coverage of 290 to 400 nm)
  A critical wavelength λc strictly greater than 370 nm, which allows better covering the long part of UVA with regard to the filters currently used on the market.
  Containing the minimum number and concentration of filters for a better tolerance and toxicity response.
  Being photostable (no degradation of the filtering system under UV irradiation)
  Being stable to light, air, humidity and temperature.
  Meeting toxicological requirements (perfect tolerance, nontoxic, non-mutagenic, not an endocrine disruptor, etc.).
  Having a flawless application form (not sticky, not white, pleasant feel, thus facilitating the application of the photoprotector).

The novel photoprotective system according to the invention will meet the current regulations: SPF/UVA ratio less than or equal to 3, among other things.

In one particular embodiment, the novel photoprotective system according to the invention will address the photoprotective system corresponding to the maximum category (SPF 50+).

In another particular embodiment, the novel photoprotective system according to the invention will be such that the SPF/UVA ratio will be less than or equal to 2.5.

"Photostabilization, photostable or photostability" mean, in the sense of the present invention, that after irradiation of 5 MED and preferably 10 MED, the following is retained:
- at least 80% and preferably at least 85% and even more preferentially at least 90% of the total SPF (290 to 400 nm); and
- at least 80% and preferably at least 85% and even more preferentially at least 90% for the UVA part (320 to 400 nm) of the total SPF.

While actively researching the optimization of photoprotective systems meeting the current regulations, the applicant surprisingly and unexpectedly found that the objectives outlined above were achieved with a topical, cosmetic or pharmaceutical composition containing a combination of 3 or 4 solar filters comprising:
 one or two UVA filters to obtain a critical wavelength>370 nm, chosen from among:
  i. 5,6,5,6-tetraphenyl-3,3'-(1,4-phenylene)-bis[1,2,4]triazine,
  ii. 1,1'-(1,4-piperazinediyl)bis[1-[2-[4-(diethylamino)-2-hydroxybenzoyl]phenyl]-methanone,
  iii. Butyl Methoxydibenzoylmethane (BMDBM),
  iv. Hexyl 2-[4-(diethylamino)-2-hydroxybenzoyl]benzoate,
 2,4-Bis[4-(2-ethylhexyloxy)-2-hydroxyphenyl]-6-(4-methoxyphenyl)-1,3,5-triazine=(BEMT),
 one or two filters chosen from among UVB filters, except octocrylene, PABA and ethylhexyl methoxycinnamate, said composition also containing a pharmaceutically or cosmetically acceptable excipient.

Preferably, the combination of 3 or 4 solar filters according to the invention comprises one or two UVB filters except for octocrylene, PABA and its derivatives, the cinnamate chemical family including ethylhexyl methoxycinnamate, homosalate, the benzophenone chemical family and the benzylidene camphor chemical family.

Butyl Methoxydibenzoylmethane (BMDBM) is not a UV radiation stable filter. A cleavage of the molecule takes place, which breaks down into various chemical elements with no absorbent activity. Therefore, in order to solve the problem of photostabilizing this filter, the quantity of BMDBM in the composition according to the invention will be less than 2% by weight with regard to the total weight of the composition.

In one particular embodiment of the invention, the quantity will be less than or equal to 1.5% by weight with regard to the total weight of the composition.

In another particular embodiment of the invention, the quantity will be less than 1% by weight with regard to the total weight of the composition.

Advantageously, the composition according to the invention is characterized in that the quantity of all the compounds of said combination of solar filters is less than 20%, preferably less than 16%, and even more preferentially less than 14% by weight with regard to the total weight of the composition.

Currently existing solar filters are broken down into:
 organic fat or water soluble filters that mostly absorb radiation,
 mineral sunscreens that mostly reflect radiation,
 organic sunscreens that both absorb and reflect radiation.

The list of UVA filters usable according to the invention is composed of:
 organic filters: BMDBM and hexyl 2-[4-(diethylamino)-2-hydroxybenzoyl]benzoate;
 organic sunscreens: 5,6,5,6-tetraphenyl-3,3'-(1,4-phenylene)-bis[1,2,4]triazine and 1,1'-(1,4-piperazinediyl)bis[1-[2-[4-(diethylamino)-2-hydroxybenzoyl]phenyl]-methanone The list of UVB filters is composed of:
 organic filters: Diethylhexyl Butamido Triazone and ethylhexyl triazone, Ethylhexyl Salicylate and phenylbenzimidazole sulfonic acid
 organic sunscreen: tris-biphenyl triazine.
 mineral sunscreen TiO2.

Currently, there are two broad spectrum filters on the market: BEMT and MBBT. They are filters absorbing both UVA and UVB wavelength regions. BEMT is an organic filter and MBBT is an organic sunscreen.

BEMT is a filter necessarily present in our compositions according to the invention.

In one particular embodiment of the invention and within the limit of 3 or 4 solar filters total in the composition, said composition will also comprise the broad spectrum filter MBBT.

The invention concerns the following photoprotective systems in particular:
5,6,5,6-tetraphenyl-3,3'-(1,4-phenylene)-bis[1,2,4]triazine, BEMT and tris-biphenyl triazine;
5,6,5,6-tetraphenyl-3,3'-(1,4-phenylene)-bis[1,2,4]triazine, BEMT, tris-biphenyl triazine and Diethylhexyl Butamido Triazone;
5,6,5,6-tetraphenyl-3,3'-(1,4-phenylene)-bis[1,2,4]triazine, BEMT, MBBT and Diethylhexyl Butamido Triazone;
5,6,5,6-tetraphenyl-3,3'-(1,4-phenylene)-bis[1,2,4]triazine, BMDBM, BEMT and tris-biphenyl triazine;
5,6,5,6-tetraphenyl-3,3'-(1,4-phenylene)-bis[1,2,4]triazine, hexyl 2-[4-(diethylamino)-2-hydroxybenzoyl]benzoate, BEMT and tris-biphenyl triazine;
5,6,5,6-tetraphenyl-3,3'-(1,4-phenylene)-bis[1,2,4]triazine, BEMT, tris-biphenyl triazine and TiO2,
1,1'-(1,4-piperazinediyl)bis[1-[2-[4-(diethylamino)-2-hydroxybenzoyl]phenyl]-methanone, BEMT and tris-biphenyl triazine
1,1'-(1,4-piperazinediyl)bis[1-[2-[4-(diethylamino)-2-hydroxybenzoyl]phenyl]-methanone, BEMT, tris-biphenyl triazine and ethylhexyl salicylate.

In one embodiment of the invention, the applicant proposes photoprotective systems with a minimum of organic filters and therefore photoprotective systems favoring organic and/or mineral sunscreens.

Preferably, said combination comprises at most 3 organic filters and preferably at most 2 organic filters, and even more preferentially, a single organic filter.

Organic and mineral sunscreens have a very good toxicological profile. Indeed, in view of their physical form and molecular weight, these components remain on the surface of the skin, which limits any percutaneous absorption and improves the safety of the photoprotective system.

One very noteworthy point of the present invention is the fact that said association is characterized in that it comprises at most 4 filters in all and preferably at most 3 filters.

According to one characteristic of the invention, the UVA solar filter is 5,6,5,6-tetraphenyl-3,3'-(1,4-phenylene)-bis[1,2,4]triazine combined with another UVA filter chosen from among:

1,1'-(1,4-piperazinediyl)bis[1-[2-[4-(diethylamino)-2-hydroxybenzoyl]phenyl]-methanone
BMDBM and
hexyl 2-[4-(diethylamino)-2-hydroxybenzoyl]benzoate.

According to another characteristic of the invention, the UVA solar filter is 1,1'-(1,4-piperazinediyl)bis[1-[2-[4-(diethylamino)-2-hydroxybenzoyl]phenyl]-methanone combined with another UVA filter chosen from among:
5,6,5,6-tetraphenyl-3,3'-(1,4-phenylene)-bis[1,2,4]triazine
BMDBM and
hexyl 2-[4-(diethylamino)-2-hydroxybenzoyl]benzoate.

According to another characteristic of the invention, the 5,6,5,6-tetraphenyl-3,3'-(1,4-phenylene)-bis[1,2,4]triazine content is comprised between 1% and 5% by weight with regard to the total weight of the composition.

According to another characteristic of the invention, the 1,1'-(1,4-piperazinediyl)bis[1-[2-[4-(diethylamino)-2-hydroxybenzoyl]phenyl]-methanone content is comprised between 1% and 5% by weight with regard to the total weight of the composition.

According to another characteristic of the invention, the hexyl 2-[4-(diethylamino)-2-hydroxybenzoyl]benzoate content is comprised between 1% and 10% by weight with regard to the total weight of the composition, preferably between 1 and 6%.

According to another characteristic of the invention, the BEMT content is comprised between 1% and 4% by weight with regard to the total weight of the composition.

According to another characteristic of the invention, the combination of 3 or 4 solar filters comprises one or two UVB filters except for octocrylene, PABA and its derivatives, the cinnamate chemical family including ethylhexyl methoxycinnamate, homosalate, the benzophenone chemical family and the benzylidene camphor chemical family.

According to another characteristic of the invention, the UVB filter is chosen from among the following compounds:
diethylhexyl butamido triazone
ethylhexyl triazone,
tris-biphenyl triazine.
ethylhexyl salicylate
phenylbenzimidazole sulfonic acid
TiO2.

According to another characteristic of the invention, the tris-biphenyl triazine content is comprised between 3% and 7% by weight with regard to the total weight of the composition.

According to another characteristic of the invention, the diethylhexyl butamido triazone content is comprised between 1% and 5% by weight with regard to the total weight of the composition.

According to another characteristic of the invention, the ethylhexyl triazone content is comprised between 1% and 5% by weight with regard to the total weight of the composition.

According to another characteristic of the invention, the TiO2 content is comprised between 1% and 10% by weight with regard to the total weight of the composition.

The composition according to the invention also comprises the broad spectrum filter MBBT.

According to another characteristic of the invention, the combination of solar filters consists of 5,6,5,6-tetraphenyl-3,3'-(1,4-phenylene)-bis[1,2,4]triazine, BEMT and tris-biphenyl triazine.

According to another characteristic of the invention, the combination of solar filters consists of 5,6,5,6-tetraphenyl-3,3'-(1,4-phenylene)-bis[1,2,4]triazine, BEMT, tris-biphenyl triazine and Diethylhexyl Butamido Triazone.

According to another characteristic of the invention, the combination of solar filters consists of 5,6,5,6-tetraphenyl-3,3'-(1,4-phenylene)-bis[1,2,4]triazine, BEMT, tris-biphenyl triazine and BMDBM.

According to another characteristic of the invention, the combination of solar filters consists of 5,6,5,6-tetraphenyl-3,3'-(1,4-phenylene)-bis[1,2,4]triazine, BEMT, MBBT and Diethylhexyl Butamido Triazone.

According to another characteristic of the invention, the combination of solar filters consists of 5,6,5,6-tetraphenyl-3,3'-(1,4-phenylene)-bis[1,2,4]triazine, hexyl 2-[4-(diethylamino)-2-hydroxybenzoyl]benzoate, BEMT and tris-biphenyl triazine.

According to another characteristic of the invention, the combination of solar filters consists of 5,6,5,6-tetraphenyl-3,3'-(1,4-phenylene)-bis[1,2,4]triazine, BEMT, tris-biphenyl triazine and TiO2.

According to another characteristic of the invention, the combination of solar filters consists of 1,1'-(1,4-piperazinediyl)bis[1-[2-[4-(diethylamino)-2-hydroxybenzoyl]phenyl]-methanone, BEMT and tris-biphenyl triazine.

According to another characteristic of the invention, the combination of solar filters consists of 1,1'-(1,4-piperazinediyl)bis[1-[2-[4-(diethylamino)-2-hydroxybenzoyl]phenyl]-methanone, BEMT, tris-biphenyl triazine and ethylhexyl salicylate.

The present invention also concerns topical compositions containing the combination such as previously described for their photoprotective use, notably for skin and/or hair.

"Pharmaceutically or cosmetically acceptable excipient" means any adjuvant or excipient for manufacturing, preserving or administering the composition.

Compositions according to the invention may more particularly be sunscreen compositions. They are particularly intended for protecting skin (face and/or body) and/or hair from ultraviolet radiation.

The present invention also concerns a method for protecting skin (face and/or body) and/or hair from ultraviolet radiation comprising applying a composition described previously onto the skin (face and/or body) and/or hair.

Compositions according to the invention may also comprise conventional cosmetic or pharmaceutical adjuvants, in particular chosen from among fats, organic solvents, thickeners, softeners, opacifiers, stabilizers, emollients, antifoaming agents moisturizers, fragrances, preservatives, polymers, fillers, sequestering agents, bactericides, odor absorbers, basifying or acidifying agents, surfactants, free-radical scavengers, antioxidants, vitamins E and C, alpha-hydroxy acids or any other ingredient usually used in cosmetics or pharmaceuticals, particularly for the manufacture of sunscreen compositions.

The fats may consist of an oil or wax or mixtures thereof, and they also include fatty acids, fatty alcohols and fatty acid esters. The oils may be chosen from among animal, vegetable, mineral or synthetic oils and notably Vaseline oil, paraffin oil, volatile or nonvolatile silicone oil, isoparaffins, polyolefins and fluorinated and perfluorinated oils. Likewise, waxes may be chosen from among animal, fossil, vegetable or synthetic waxes such as beeswax, candelilla wax, carnauba wax, petroleum wax (or microcrystalline wax), paraffin, and mixtures thereof.

The composition may further comprise a water-miscible polyol at room temperature (around 25° C.), in particular chosen from among polyols having from 2 to carbon atoms, preferably having 2 to 10 carbon atoms, and preferentially having 2 to 6 carbon atoms, such as glycerin; glycol derivatives such as propylene glycol, butylene glycol, pentylene glycol, hexylene glycol, dipropylene glycol and diethylene glycol; glycol ethers such as C1-C4 alkyl ethers of mono-, di- or tri-propylene glycol, C1-C4 alkyl ethers of mono-, di- or triethylene glycol and mixtures thereof.

The composition may also comprise thickeners or rheology modifying agents, such as, for example, nonionic ethoxylated hydrophobically modified urethanes, polycarboxylic acid thickeners such as acrylates/steareth 20 methacrylate copolymers, carbomers, crosslinked acrylate copolymers and mixtures thereof.

The composition may also comprise acids and bases to adjust the pH zone of said composition. The bases may be mineral (sodium hydroxide, potassium hydroxide, ammonia, etc.) or organic such as mono-, di- or triethanolamine, aminomethylpropanediol, N-methylglucamine, basic amino acids such as arginine and lysine, and mixtures thereof.

The composition may also comprise skin conditioners. Examples of skin conditioners include, but are not limited to, anionic, cationic and nonionic surfactants such as sodium lauryl sulfate, sodium dioctyl sulfosuccinate, sodium stearate, ester sorbitan, ethoxylated fatty acids, ethoxylated fatty alcohols such as trideceth-9 and PEG-5 ethylhexanoate; any other emulsifier and conditioning agent known to the skilled person, and mixtures thereof.

Compositions according to the invention may further comprise additional active agents chosen in particular from among from moisturizers, desquamating agents, agents for improving barrier function, depigmenting agents, antioxidants, skin tighteners, anti-glycation agents, agents stimulating the synthesis of dermal and/or epidermal macromolecules and/or preventing their degradation, agents stimulating fibroblast or keratinocyte proliferation and/or keratinocyte differentiation, NO synthase inhibitors, agents increasing the activity of the sebaceous gland, tensioning agents, lipo-restructuring agents, slimming agents, agents promoting skin microcirculation, soothing and/or irritant agents, sebo-regulating or anti-seborrheic agents, astringents, wound healing agents, anti-inflammatory agents, anti-acne agents, and mixtures thereof.

Compositions according to the invention may be presented in any appropriate form for topical application, especially on the skin and/or hair. In particular, they may be present in the form of emulsions obtained by dispersing a fatty phase in an aqueous phase, for example one or multiple oil-in-water or water-in-oil emulsions, or in the form of a gel or an anhydrous liquid, pasty or solid product, or in the form of a dispersion in the presence of spherules. Compositions according to the invention may also be less fluid and may be in the form of a white or colored cream, ointment, milk, lotion, serum, paste, mask, powder, solid stick or optionally, an aerosol, foam or spray. These compositions may also be water resistant.

EVALUATION AND EXAMPLES OF COMPOSITION

In vitro Method of Evaluating Total UV and UVA Photostability

A) Material

UV Spectrophotometer:

The spectrophotometer measures the spectral transmittance through a plate with and without a layer of a sunscreen composition on its surface.

The spectrophotometer should allow measurements comprised between 290 nm and 400 nm. To reduce variability between measurement readings and to compensate for the lack of uniformity of the product layer, it is recommended that the reading zone of the sites be at least 0.5 cm².

The spectrophotometer used for these measurements is the Labsphere® UV-1000S or 2000S.

Plate:

The plate is the material onto which the sunscreen composition is applied. This material must be transparent to UV, non-fluorescent, photostable and inert with regard to the compounds of the compositions tested. For this protocol, polymethyl methacrylate (PMMA) plates proved ideal.

UV Source:

The UV source is a solar simulator with a xenon arc lamp diffusing a visible+UVA+UVB spectrum. The UV source used for this study is Suntest CPS+ (Atlas).

B) Method:

Measuring Transmission Through an Untreated Plate:

Firstly, it is necessary to determine UV transmission through a control plate. This is prepared by spreading a few microliters of glycerin so that the surface of the plate is completely covered.

Sample Application:

The sample to be tested is applied onto the PMMA plate in an amount of 1.3 mg/cm² (actual quantity remaining on the plate). To guarantee the accuracy of the amount and the reproducibility of the results, the application zone is larger than 10 cm².

The sample to be tested is applied in the form of a large number of small drops of the same volume, distributed over the entire surface of the plate.

In order to ensure that the quantity of the product is correct, a method of validating the quantity of product applied must be adopted (for example: weigh the plate before and after application of the product).

After application of the defined quantity of sample, the sample should be spread over the entire plate as quickly as possible (less than 30 seconds).

The sample is then placed for 15 minutes in the dark at room temperature in order to promote the formation of a homogenous film.

Measuring Transmission Through a Plate Treated with a Sample:

The plate treated with the sample is analyzed with the spectrophotometer and the mean value of UV radiation transmission through the sample is determined for each wavelength from 290 nm to 400 nm (using the monochromatic absorbance data measured on the different areas of the plate).

Number of Measurements:

At least three PMMA plates should be prepared for each sample. Each plate should be measured in at least nine different regions unless almost the entire surface is measured by spectrophotometry.

C) Calculation of Photostability:

Calculation of SPF and UVA (PPD) in vitro from absorbance data $A(\lambda)$ before and after irradiation with doses of 5 and 10 MED.

$$SPF \text{ in vitro} = \frac{\int_{\lambda=290 \, nm}^{\lambda=400 \, nm} E(\lambda) * S(\lambda) * d\lambda}{\int_{\lambda=290 \, nm}^{\lambda=400 \, nm} E(\lambda) * S(\lambda) * 10^{-A(\lambda)} * d\lambda}$$

Wherein:

E(λ)=Erythemal effectiveness spectrum

S(λ)=Solar spectral irradiance

A(λ)=Sample absorbance dλ=Wavelength variation (1 nm)

$$PPD \text{ in vitro} = \frac{\int_{\lambda=320 \, nm}^{\lambda=400 \, nm} P(\lambda) * I(\lambda) * d\lambda}{\int_{\lambda=320 \, nm}^{\lambda=400 \, nm} P(\lambda) * I(\lambda) * 10^{-A(\lambda)} * d\lambda}$$

Wherein:

P(λ)=PPD action spectrum (Persistent Pigment Darkening)

I (λ)=Solar spectral irradiance

A (λ)=Sample absorbance dλ=Wavelength variation (1 nm)

Calculation of photostability from the following formulas:

$$\text{Total } UV \text{ photostability} = \frac{SPF \text{ before irradiation}}{SPF \text{ after irradiaton}}$$

$$UVA \text{ photostability} = \frac{PPD \text{ before irradiation}}{PPD \text{ after irradiation}}$$

In vitro Method for Evaluating COLIPA UVA and Critical Wavelength:

In vitro COLIPA UVA and critical wavelength are determined according to the COLIPA method, Guidelines March 2011.

Example 1

| Ingredients | % |
|---|---|
| 5,6,5,6-tetraphenyl-3,3'-(1,4-phenylene)-bis[1,2,4]triazine | 4 |
| Bis-Ethylhexyloxyphenol Methoxyphenyl Triazine | 3 |
| Tris-biphenyl triazine | 5 |
| Glycerin | 10.0 |
| Demineralized water | QSP 100 |
| Na2EDTA | 0.1 |
| Xanthan gum | 0.3 |
| C12-C15 alkyl benzoate | 10.0 |
| Octyl palmitate | 5.0 |
| Preservatives | qs |
| Stearyl alcohol | 2.5 |
| Glycerol monostearate | 2.5 |
| Potassium cetyl phosphate | 1.8 |

Results

| Parameter measured: | Composition 1 |
|---|---|
| SPF in vitro | 66 |
| COLIPA UVA | 27.4 |
| Critical wavelength nm | 378 |
| UVA photostability 5 MED | 100% |
| Total UV photostability 5 MED | 100% |

Example 2

| Ingredients | % |
|---|---|
| 5,6,5,6-tetraphenyl-3,3'-(1,4-phenylene)-bis[1,2,4]triazine | 4 |
| Bis-Ethylhexyloxyphenol Methoxyphenyl Triazine | 3 |
| Methylene Bis-Benzotriazolyl Tetramethylbutylphenol | 4 |
| Diethylhexyl Butamido Triazone | 2 |
| Glycerin | 10.0 |
| Demineralized water | QSP 100 |
| Na2EDTA | 0.1 |
| Xanthan gum | 0.3 |
| C12-C15 alkyl benzoate | 10.0 |
| Octyl palmitate | 5.0 |
| Preservatives | qs |
| Stearyl alcohol | 2.5 |
| Glycerol monostearate | 2.5 |
| Potassium cetyl phosphate | 1.8 |

Results

| Parameter measured: | Composition 2 |
|---|---|
| SPF in vitro | 50.6 |
| COLIPA UVA | 28.7 |
| Critical wavelength nm | 380 |
| UVA photostability 5 MED | 100% |
| Total UV photostability 5 MED | 100% |

Example 3

| Ingredients | % |
|---|---|
| 5,6,5,6-tetraphenyl-3,3'-(1,4-phenylene)-bis[1,2,4]triazine | 3 |
| BMDBM | 1 |
| Bis-Ethylhexyloxyphenol Methoxyphenyl Triazine | 3 |
| Tris-biphenyl triazine | 5 |
| Glycerin | 10.0 |
| Demineralized water | QSP 100 |
| Na2EDTA | 0.1 |
| Xanthan gum | 0.3 |
| C12-C15 alkyl benzoate | 10.0 |
| Octyl palmitate | 5.0 |
| Preservatives | qs |
| Stearyl alcohol | 2.5 |
| Glycerol monostearate | 2.5 |
| Potassium cetyl phosphate | 1.8 |

Results

| Parameter measured: | Composition 3 |
|---|---|
| SPF in vitro | 86.3 |
| COLIPA UVA | 31.2 |
| Critical wavelength nm | 378 |
| UVA photostability 5 MED | 93% |
| Total UV photostability 5 MED | 100% |

Example 4

| Ingredients | % |
| --- | --- |
| 1,1'-(1,4-piperazinediyl)bis[1-[2-[4-(diethylamino)-2-hydroxybenzoyl]phenyl]-methanone | 2.5 |
| Bis-Ethylhexyloxyphenol Methoxyphenyl Triazine | 4 |
| Tris-biphenyl triazine | 5 |
| Glycerin | 10.0 |
| Demineralized water | QSP 100 |
| Na2EDTA | 0.1 |
| Xanthan gum | 0.3 |
| C12-C15 alkyl benzoate | 10.0 |
| Octyl palmitate | 5.0 |
| Preservatives | qs |
| Stearyl alcohol | 2.5 |
| Glycerol monostearate | 2.5 |
| Potassium cetyl phosphate | 1.8 |

The invention claimed is:

1. A topical, cosmetic or pharmaceutical composition comprising one or more pharmaceutically or cosmetically acceptable excipients and a combination of solar filters only consisting of 3 or 4 solar filters comprising:
   one or two solar UVA filters to obtain a critical wavelength>370 nm, chosen from among:
   i. 5,6,5,6-tetraphenyl-3,3'-(1,4-phenylene)-bis[1,2,4]triazine,
   ii. 1,1'-(1,4-piperazinediyl)bis[1-[2-[4-(diethylamino)-2-hydroxybenzoyl[phenyl]-methanone,
   iii. Butyl Methoxydibenzoylmethane (BMDBM), in a quantity less than 2% by weight with regard to the total weight of said composition,
   iv. Hexyl 2-[4-(diethylamino)-2-hydroxybenzoyl]benzoate, with the proviso that 5,6,5,6-tetraphenyl-3,3'-(1,4-phenylene)-bis[1,2,4]triazine is necessarily present,
   2,4-Bis[4-(2-ethylhexyloxy)-2-hydroxyphenyl]-6-(4-methoxyphenyl)-1,3,5-triazine (BEMT), and
   one or two solar filters chosen from among solar UVB filters, with the proviso that the solar filters do not include octocrylene, para-aminobenzoic acid (PABA) and ethylhexyl methoxycinnamate.

2. The composition according to claim 1, wherein the quantity of all the compounds of said combination of solar filters is less than 20% by weight with regard to the total weight of the topical composition.

3. The composition according to claim 1, wherein said one or two solar UVA filters are two UVA solar filters consisting of 5,6,5,6-tetraphenyl-3,3'-(1,4-phenylene)-bis[1,2,4]triazine combined with another UVA filter chosen from among:
   1,1'-(1,4-piperazinediyl)bis[1-[2-[4-(diethylamino)-2-hydroxybenzoyl[phenyl]-methanone,
   BMDBM, and
   hexyl 2-[4-(diethylamino)-2-hydroxybenzoyl]benzoate.

4. The composition according to claim 1, wherein said one or two solar UVA filters are two UVA solar filters consisting of 1,1'-(1,4-piperazinediyl)bis[1-[2-[4-(diethylamino)-2-hydroxybenzoyl]phenyl]-methanone combined with:
   5,6,5,6-tetraphenyl-3,3'-(1,4-phenylene)-bis[1,2,4]triazine.

5. The composition according to claim 1, wherein the 5,6,5,6-tetraphenyl-3,3'-(1,4-phenylene)-bis[1,2,4]triazine content is between 1% and 5% by weight with regard to the total weight of the composition.

6. The composition according to claim 1, wherein the 1,1'-(1,4-piperazinediyl)bis[1-[2-[4-(diethylamino)-2-hydroxybenzoyl]phenyl]-methanone content is between 1% and 5% by weight with regard to the total weight of the composition.

7. The composition according to claim 1, wherein the hexyl 2-[4-(diethylamino)-2-hydroxybenzoyl]benzoate content is between 1% and 10% by weight with regard to the total weight of the composition.

8. The composition according to claim 1, wherein the BEMT content is between 1% and 4% by weight with regard to the total weight of the composition.

9. The composition according to claim 1, wherein the combination of 3 or 4 solar filters comprises one or two solar UVB filters with the proviso that the solar filters do not include octocrylene, PABA and its derivatives, the cinnamate chemical family including ethylhexyl methoxycinnamate, homosalate, the benzophenone chemical family and the benzylidene camphor chemical family.

10. The composition according to claim 1, wherein said solar UVB filter is chosen from among the following compounds:
    diethylhexyl butamido triazone,
    ethylhexyl triazone,
    tris-biphenyl triazine,
    ethylhexyl salicylate,
    phenylbenzimidazole sulfonic acid and
    $TiO_2$.

11. The composition according to claim 10, wherein the tris-biphenyl triazine content is between 3% and 7% by weight with regard to the total weight of the composition.

12. The composition according to claim 10, wherein the diethylhexyl butamido triazone content is between 1% and 5% by weight with regard to the total weight of the composition.

13. The composition according to claim 10, wherein the ethylhexyl triazone content is between 1% and 5% by weight with regard to the total weight of the composition.

14. The composition according to claim 10, wherein the $TiO_2$ content is between 1% and 10% by weight with regard to the total weight of the composition.

15. The composition according to claim 1, wherein it also comprises the broad spectrum filter methylene bis-benzotriazolyl tetramethylbutyl-phenol (MBBT).

16. The composition according to claim 1, wherein the combination of solar filters consists of 5,6,5,6-tetraphenyl-3,3'-(1,4-phenylene)-bis[1,2,4]triazine, BEMT and tris-biphenyl triazine.

17. The composition according to claim 1, wherein the combination of solar filters consists of 5,6,5,6-tetraphenyl-3,3'-(1,4-phenylene)-bis[1,2,4]triazine, BEMT, tris-biphenyl triazine and diethylhexyl butamido triazone.

18. The composition according to claim 1, wherein the combination of solar filters consists of 5,6,5,6-tetraphenyl-3,3'-(1,4-phenylene)-bis[1,2,4]triazine, BEMT, tris-biphenyl triazine and BMDBM.

19. The composition according to claim 1, wherein the combination of solar filters consists of 5,6,5,6-tetraphenyl-3,3'-(1,4-phenylene)-bis[1,2,4]triazine, BEMT, MBBT and diethylhexyl butamido triazone.

20. The composition according to claim 1, characterized in that it contains 3 solar filters in all.

21. The composition according to claim 1, characterized in that it contains 4 solar filters in all.

22. A method for photoprotecting skin and/or hair, said method comprising:

applying on the skin and/or hair the composition according to claim 1.

23. The composition according to claim 1, wherein the quantity of all the compounds of said combination of solar filters is less than 16% by weight with regard to the total weight of the topical composition.

24. The composition according to claim 1, wherein the quantity of all the compounds of said combination of solar filters is less than 14% by weight with regard to the total weight of the topical composition.

25. The composition according to claim 1, wherein the hexyl 2-[4-(diethylamino)-2-hydroxybenzoyl]benzoate content is between 1% and 6%.

* * * * *